(12) United States Patent
Horstmann et al.

(10) Patent No.: US 10,772,845 B2
(45) Date of Patent: Sep. 15, 2020

(54) TRANSDERMAL THERAPEUTIC SYSTEM FOR THE ADMINISTRATION OF PEPTIDES

(75) Inventors: Michael Horstmann, Neuwied (DE); Horst Dzekan, Meinborn (DE); Sandra Wiedersberg, Steigra (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 13/512,403

(22) PCT Filed: Dec. 2, 2010

(86) PCT No.: PCT/EP2010/007322
§ 371 (c)(1),
(2), (4) Date: May 29, 2012

(87) PCT Pub. No.: WO2011/066970
PCT Pub. Date: Jun. 9, 2011

(65) Prior Publication Data
US 2012/0245538 A1  Sep. 27, 2012

(30) Foreign Application Priority Data
Dec. 4, 2009 (DE) .......................... 10 2009 056 746

(51) Int. Cl.
*A61K 38/09* (2006.01)
*A61K 9/70* (2006.01)
*A61K 38/095* (2019.01)

(52) U.S. Cl.
CPC ............ *A61K 9/7084* (2013.01); *A61K 38/09* (2013.01); *A61K 38/095* (2019.01); *Y10T 156/1089* (2015.01)

(58) Field of Classification Search
CPC ...... A61K 38/09; A61K 38/11; A61K 9/0784; A61K 9/7092; A61K 9/7023; A61K 9/7053; A61K 9/7061; A61K 9/7084; A61K 9/7069; A61L 15/44
USPC .................. 604/290, 304, 307; 424/447–449
See application file for complete search history.

(56) References Cited

U.S. PATENT DOCUMENTS

| 3,598,122 | A | * | 8/1971 | Zaffaroni | ...................... 424/435 |
| 3,797,494 | A | * | 3/1974 | Zaffaroni | ...................... 424/434 |
| 4,140,115 | A | * | 2/1979 | Schonfeld | ............... A61L 15/58 |
| | | | | | 428/411.1 |
| 4,616,644 | A | * | 10/1986 | Saferstein et al. | .............. 602/48 |

(Continued)

FOREIGN PATENT DOCUMENTS

| JP | 2004-520152 A | 7/2004 |
| JP | 2004-538345 A | 12/2004 |

(Continued)

OTHER PUBLICATIONS

Tan et al. ("Pressure-sensitive adhesives for transdermal drug delivery systems," PSTT vol. 2, No. 2 Feb. 1999, pp. 60-69).*

(Continued)

*Primary Examiner* — Ariana Zimbouski
(74) *Attorney, Agent, or Firm* — ProPat, LLC

(57) ABSTRACT

The invention relates to a transdermal therapeutic system (TTS) which is suited for the administration of a peptide to a patient through skin treated with ablation. The transdermal therapeutic system incorporates a back layer and an active substance-containing layer that includes at least one peptide and a carrier substance.

30 Claims, 2 Drawing Sheets

(56) References Cited

U.S. PATENT DOCUMENTS

| | | | | |
|---|---|---|---|---|
| 4,834,978 | A * | 5/1989 | Nuwayser | 424/448 |
| 5,132,115 | A * | 7/1992 | Wolter | A45D 34/00 |
| | | | | 424/448 |
| 5,225,473 | A * | 7/1993 | Duan | A61B 5/04087 |
| | | | | 522/167 |
| 5,230,898 | A * | 7/1993 | Horstmann et al. | 424/449 |
| 5,716,636 | A * | 2/1998 | Horstmann et al. | 424/448 |
| 6,225,521 | B1 * | 5/2001 | Gueret | A61K 8/0208 |
| | | | | 602/41 |
| 6,264,979 | B1 * | 7/2001 | Svedman | 424/449 |
| 6,814,976 | B1 * | 11/2004 | Hille | A61K 9/7084 |
| | | | | 424/443 |
| 6,967,261 | B1 * | 11/2005 | Soerens et al. | 602/48 |
| 7,691,404 | B2 * | 4/2010 | Song et al. | 424/448 |
| 2002/0038101 | A1 * | 3/2002 | Avrahami et al. | 604/20 |
| 2002/0128285 | A1 * | 9/2002 | Cassel | 514/304 |
| 2003/0104041 | A1 * | 6/2003 | Hsu | A61K 8/0208 |
| | | | | 424/449 |
| 2003/0125680 | A1 * | 7/2003 | Ding | 604/304 |
| 2004/0033254 | A1 | 2/2004 | Song et al. | |
| 2006/0034904 | A1 * | 2/2006 | Weimann | A61K 9/0009 |
| | | | | 424/449 |
| 2006/0078604 | A1 * | 4/2006 | Kanios | A61K 9/7061 |
| | | | | 424/449 |
| 2007/0081977 | A1 * | 4/2007 | Horstmann | A61K 9/0021 |
| | | | | 424/93.2 |
| 2008/0280819 | A1 * | 11/2008 | Mulugeta et al. | 514/9 |
| 2009/0010998 | A1 * | 1/2009 | Marchitto | A61K 9/7084 |
| | | | | 424/449 |
| 2009/0208560 | A1 * | 8/2009 | Aida | A61K 9/7084 |
| | | | | 424/448 |
| 2009/0264806 | A1 * | 10/2009 | Tamura | A61K 9/7053 |
| | | | | 602/48 |
| 2010/0292149 | A1 * | 11/2010 | Bowser | 514/10.9 |
| 2011/0190332 | A1 * | 8/2011 | Mailman | 514/284 |

FOREIGN PATENT DOCUMENTS

| | | |
|---|---|---|
| WO | WO 95/30410 A2 | 11/1995 |
| WO | WO 2005/042054 A2 | 5/2005 |
| WO | WO 2007/039646 A1 | 4/2007 |
| WO | WO 2010/0028412 A2 | 8/2008 |

OTHER PUBLICATIONS

PubChem: Vasopressin, https://pubchem.ncbi.nlm.nih.gov/compound/argipressin#section=Top, p. 1, accessed May 22, 2018.*
PubChem: Triptorelin, https://pubchem.ncbi.nlm.nih.gov/compound/triptorelin, p. 1, accessed May 22, 2018.*
PubChem: Desmopressin, https://pubchem.ncbi.nlm.nih.gov/compound/16679-58-6, p. 1, accessed May 22, 2018.*

* cited by examiner

Transdermal therapeutic system with separate layer of pressure-sensitive adhesive:

Triptorelin permeation profile, in vitro permeation:

TRANSDERMAL THERAPEUTIC SYSTEM FOR THE ADMINISTRATION OF PEPTIDES

CROSS-REFERENCE TO RELATED APPLICATIONS

This application is being filed under 35 USC § 371 as a National Stage Application of pending International Application No. PCT/EP2010/007322 filed Dec. 2, 2010, which claims priority to German Patent Application No. 10 2009 056 746.1, filed Dec. 4, 2009. Both International Application No. PCT/EP2010/007322 and German Patent Application No. 10 2009 056 746.1 are herby incorporated by reference herein in their entirety.

The subject matter of the present invention is a transdermal therapeutic system (TTS) for administering peptides and other molecules of high molecular weight. Particularly suitable in this respect are those peptides which can be used as active pharmaceutical ingredients. These include, in particular, the peptide hormones.

BACKGROUND OF THE NVENTION

Transdermal therapeutic systems (TTS) as pharmaceutical administration forms have been known for a long time. For the transdermal administration of active pharmaceutical ingredients by means of TTS, the stratum corneum (SC), the outermost layer of the skin, in the majority of cases constitutes the real barrier for the permeability and for the rate of passage of the active pharmaceutical ingredient.

Peptides and proteins and also other high-molecular molecules, with a molecular weight of more than 500 daltons—such as, for example, tacrolimus, heparin, and numerous salts of betamethasone—are generally not absorbed transdermally, owing to their molecular size and to their physicochemical properties.

Moreover, the majority of peptides possess a low oral bioavailability and are subject to severe, proteolytic degradation in the gastrointestinal tract. For these reasons, peptides are commonly administered parenterally, bypassing the gastrointestinal tract. This involves injections or infusions which are administered below the skin, into the muscle or directly into the bloodstream.

The transdermal route here would offer a noninvasive alternative—with high patient compliance—to this invasive, parenteral administration. Consequently there are numerous approaches to facilitating the permeability of the skin for molecules having a molecular weight of more than 500 daltons. These approaches include, primarily, the use of permeation enhancers or the additional use of heat.

Another technique for making molecules with poor skin transit amenable to transdermal administration is to facilitate the passage of an active ingredient of this kind through the stratum corneum by partly destroying or removing this layer beforehand. These techniques, referred to as "skin ablation", use thermal or mechanical energy in order to effect partial destruction or removal of the stratum corneum and hence to create direct channels into the living epidermis. The permeability of the skin is increased and the transdermal absorption of high-molecular-weight molecules can therefore be made possible.

As a result of this pretreatment of the skin, moreover, it is also possible for hydrophilic active ingredients to be administered transdermally, the transdermal route having hitherto been closed to such ingredients on account of their hydrophilicity. Ingredients contemplated here include, for example, fentanyl citrate, granisetrone HCl, Na diclofenac, and apomorphine sulfate. Furthermore, the TTS area of existing TTS systems can be reduced significantly, for the same blood levels, by means of skin ablation pretreatment.

The skin ablation technique commonly generates a multiplicity of microchannels through the stratum corneum, and yet the percentage "perforated" proportion of the treated skin area is relatively small. A description of the laser skin ablation technique is present in WO 2007/039646, whose US equivalent is United States Patent Publication No. 2008/255034.A1.

Triptorelin is a peptide hormone having a molecular weight of 1311 Da. It is employed for the treatment of advanced prostate cancer, in endometriosis, and in premature puberty. Another area of application is in in vitro fertilization (assistive fertility therapy). For these purposes, triptorelin is available as a ready-to-inject solution (under the brand name DECAPEPTYL ®, UROPEPTYL DEPOT®), and as a dry substance with solvent for producing a suspension for injection (under the brand name PAMORELIN®). Triptorelin here is used as salt in the form of the diacetate or embonate, respectively. In a triptorelin treatment, the solution, optionally prepared by the patient shortly before administration of the solution, is administered by injection. Triptorelin therapy may last for a period of several weeks to months and may require once-daily injection.

Desmopressin is a synthetic analogue of the peptide hormone vasopressin, having a molecular weight of 1069 Da, and is used as a pharmaceutical (antidiuretic). Desmopressin is an antidiuretic. In addition there is also an indication for enuresis nocturna (bedwetting). Desmopressin can also be given as an antihemorrhagic in cases, for example, of hemophilia, uremic thrombocytopathy or Willebrand-Jürgens syndrome. For these purposes, desmopressin is available in the form of tablets (MINIRIN®), an injection solution (MINIRIN PARENTERAL®) or a nasal spray (MINIRIN®, Desmopressin TAD®).

Vasopressin is a peptide hormone having a molecular weight of 1084 Da. Vasopressin is used as a highly hypertensive substance successfully in patients in a state of shock. Diabetes insipidus centralis (ICD-10: E23.3 and N25.1) can be treated by administration of vasopressin.

The known products, however, possess certain disadvantages, which are attributable in particular to the low stability of the peptides in solution, this low stability being common knowledge.

For instance, the time for which ready-to-inject solution can be kept is only 3 weeks. The greatest disadvantage, however, is the low level of patient compliance with injection, owing to the invasive nature of the treatment. Molecules of high molecular weight have to date been closed off from transdermal administration as a result of their physicochemical properties. Transdermal administration of these molecules is made possible only by pretreatment of the skin.

In order to increase the stability and hence the time for which the peptide preparations can be kept, the injection solution is prepared not until immediately prior to administration, by mixing of the dry active ingredient (usually freeze-dried) with the solvent. The approach of allowing the injection suspension to be prepared by the patient not until shortly before its administration entails the risk of an imprecise dosing. In addition, the dispensing of powders on the industrial scale represents a task which imposes very exacting requirements on accuracy, particularly in the case of such a highly efficient active ingredient as a peptide hormone. In the pharmaceutical industry, therefore, the aim as far as possible is to avoid operating with solids.

Lastly, injection itself may be accompanied by difficulties, which lie primarily in pain during application, a risk of injury, and the risk of infections.

SUMMARY OF ADVANTAGEOUS EMODIMENTS OF THE INVENTION

It is an object of the present invention to provide a transdermal therapeutic system (TTS) for the administration of peptides and other molecules with poor skin access.

In order for the TTS to be stable on storage at room temperature and to have little susceptibility to microbes, it ought to include as little water as possible.

The TTS here is to be applied to an area of skin of which beforehand at least a subregion of the stratum corneum has been destroyed or removed.

The intention in particular is to manufacture a TTS with one of the active ingredients triptorelin, desmopressin, vasopressin or one of their pharmaceutically acceptable salts, with which peptides can be administered through the skin in therapeutic doses to a patient.

The skin is preferably to be skin which has undergone an "ablative" pretreatment, where a proportion of the stratum corneum has been removed.

The intention here is not only to avoid the route of administration by injection. The TTS itself is as far as possible to be equipped without microinjection needles, microblades and/or other needles and barbs, in order to avoid or rule out additional mechanical injury to the stratum corneum. However, where appropriate, the TTS may also be furnished with construction elements of these kinds.

It is also the intention that the peptide can be applied by means of the transdermal therapeutic system as part of a long-term application.

The product is also to be amenable to production in a simple and cost-effective way, without having to take into account the production problems typical of pulverulent administration forms.

DETAILED DESCRIPTION OF ADVANTAGEOUS EMBODIMENTS OF THE INVENTION

Figure 1:
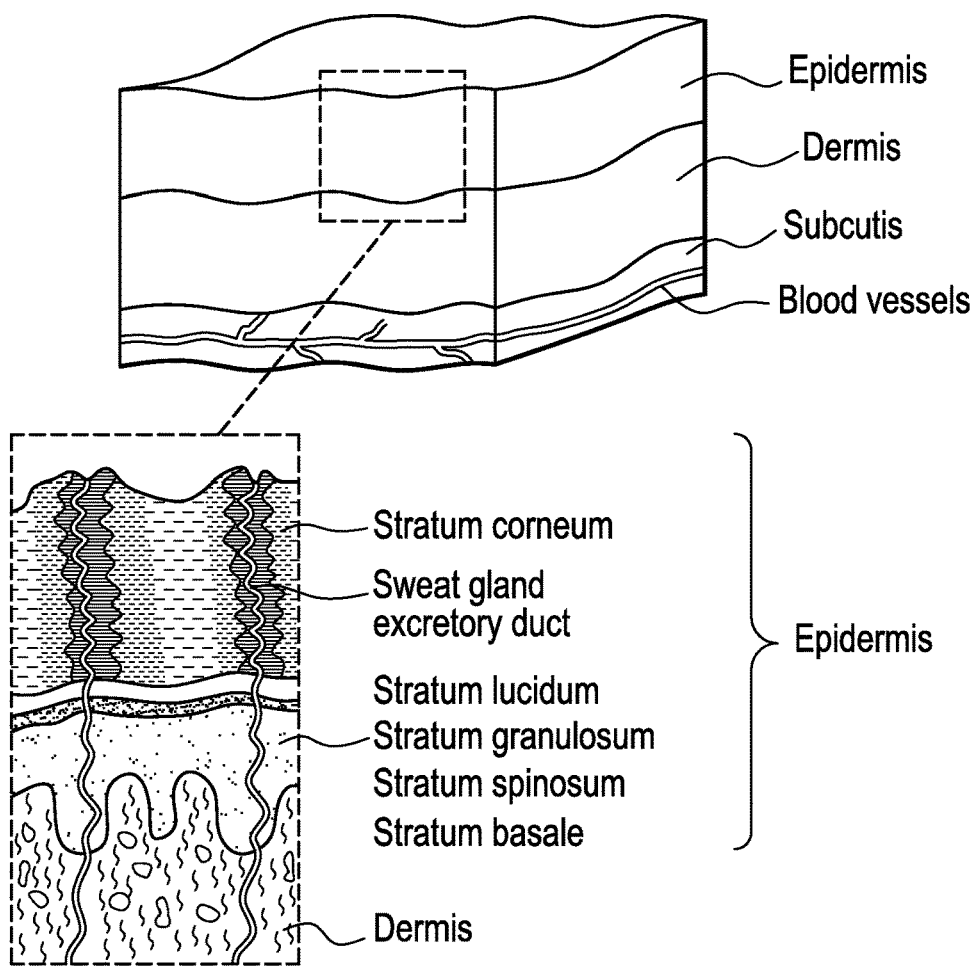
FIG. 1 is a diagrammatic stricture of intact, normal skin, with an enlarged section of the outermost layer.

The object is achieved by means of a transdermal therapeutic system (TTS) for administering peptides, which comprises at least one active ingredient layer which comprises a peptide and a preferably hydrophilic carrier substance for the peptide.

The TTS may further comprise a backing layer which is impermeable to the peptide.

The active ingredient layer, which comprises the peptide and the carrier substance for the peptide, may be pressure-sensitively adhesive.

The active ingredient layer can be produced on a full-area basis, by means of coating and drying operations that are customary for TTS.

The active ingredient layer may comprise, as the hydrophilic carrier substance, polyvinylpyrrolidone (PVP) and/or polyvinyl alcohol (PVA) and/or cellulose, and derivatives thereof. Particularly suitable is PVP, such as Kollidon 90, for example.

The at least one active ingredient layer may be admixed with plasticizers, such as glycerol, medium-chain triglycerides (MYGLIOL®) or other hydrocarbons.

The active ingredient layer may comprise further excipients that stabilize the active ingredient, preferably buffer substances or sugars.

The TTS may also comprise at least one further, additional layer of pressure-sensitive adhesive, which is substantially free from active ingredient and is pressure-sensitively adhesive. An additional layer of pressure-sensitive adhesive of this kind ensures reliable adhesion of the TTS on the skin in the event that the active ingredient layer is not, or not sufficiently, pressure-sensitively adhesive.

The TTS may comprise active peptidic ingredients, more particularly peptides having a low molecular weight of less than 2 500 Da.

In one particular embodiment, the TTS comprises the active ingredient triptorelin and/or at least one of its pharmaceutically acceptable salts.

In another particular embodiment, the TTS comprises the active ingredient desmopressin and/or at least one of its pharmaceutically acceptable salts.

In another particular embodiment, the TTS comprises the active ingredient vasopressin and/or at least one of its pharmaceutically acceptable salts.

A "transdermal therapeutic system" (TTS) is a product of laminar construction. In its simplest embodiment it consists of a backing layer, an active ingredient layer, and a protective sheet which lines the active ingredient layer before the TTS is employed. In this kind of simple construction, the active ingredient layer is preferably made pressure-sensitively adhesive. If, however, the bond strength of the active ingredient layer is not sufficient, the TTS may feature an additional layer of pressure-sensitive adhesive.

This additional layer of pressure-sensitive adhesive may be disposed between the active ingredient layer and the protective sheet.

In one preferred embodiment, the additional layer of pressure-sensitive adhesive is sited between the active ingredient layer and the backing layer. In this case, in at least one section along the side margin/margins of the active ingredient layer, the layer of pressure-sensitive adhesive protrudes beyond the active ingredient layer.

The additional layer of pressure-sensitive adhesive then ensures reliable adhesion to the skin during the application of the TTS.

The TTS may also possess a membrane which controls the rate of emergence of the active ingredient from the active ingredient layer. The membrane is therefore sited on the side of the active ingredient layer that is facing the skin during the application of the TTS.

The TTS itself may, finally, possess a needle layer, which comes directly into contact with the skin and is furnished on its bottom face with microinjection needles (i.e., hollow needles for the flow passage of active ingredient), microblades (for scoring the uppermost layers of skin), needles (for perforating the uppermost layers of skin) and/or barbs (for anchoring in the skin). In one preferred embodiment, however, the TTS is furnished without such a layer.

In another embodiment, the transdermal therapeutic system may comprise more than one active ingredient layer. These active ingredient layers may be disposed one above another (forming an at least two-layer laminate) or next to one another. In the case of a TTS of this kind having more than one active ingredient layer, the individual layers may have the same construction or different constructions. In "multilayer systems" of these kinds, however, these layers differ preferably on the basis of their composition or of the active ingredient used.

The active ingredient layer may also be present in the form of a liquid-filled pouch or liquid-filled chamber, in which the active ingredient is present in dissolved, dispersed or suspended form.

Finally, the active ingredient in the active ingredient layer may be present in liquid microresevoirs, which are in dispersion in the active ingredient layer.

With the TTS described here it is possible with preference to administer active peptide ingredients by the transdermal route. The technical teaching, however, can in principle also be utilized for other physiologically active substances, including more particularly those which have been hitherto unavailable for transdermal therapy (hydrophilic active ingredients) or possess a molecular mass of more than 500 daltons.

"Peptides", for the purposes of the present description are amino acid condensation products that are linked in acid amide fashion by peptide bonds. Where the molecules are constructed from two amino acid residues, they are also referred to as dipeptides; in the case of three or more, as tripeptides, tetra-, pentapeptides etc. Peptides having 2-10 amino acid residues are therefore generally referred to collectively as oligopeptides, those with 10-100 as polypeptides. The transition from the latter to the higher-molecular-weight proteins is, however, not precisely defined. Peptides having bonds between the pendant amino groups of diaminocarboxylic acids and pendant carboxyl groups of aminodicarboxylic acids instead of the customary peptide bonds between the α-amino group and the carboxyl group are called isopeptides; the additional bonds originating from polyfunctional amino acids such as glutamic acid, aspartic acid, lysine, and arginine are responsible for the formation of peptide network structures.

The preferred peptides include peptide hormones. These are peptides of high physiological activity which develop hormone or hormonelike effects. Generally speaking, the peptide hormones are oligopeptides and polypeptides (having up to 100 amino acids), but occasionally are also higher-molecular-weight proteins (proteohormones). These include the glandular peptide hormones of the hypophysis (e.g.: corticotrophin, follitropin, lutropin, melanotropin, prolactin, somatotropin, thyrotropin, oxytocin, vasopressin), the releasing hormones and inhibiting factors of the hypothalamus, the peptide hormones from pancreas, stomach or gut (e.g.: glucagon, insulin, somatostatin, secretin, gastrin, cholecystokinin), from the thyroid gland (e.g. $^H$calcitonin, parathyrin). Certain oligopeptides have not only a conventional hormone activity but also growth factor activity, neurotransmitter activity or neuromodulator activity (mediators). Examples of such include the endogenous opiates, enkephalins and endorphins.

The peptides can be used preferably in the form of a pharmaceutically acceptable salt.

Classed among the peptides in the sense of this description are not only natural peptides and peptide hormones but also nature-identical and/or modified (that is, produced synthetically) peptides and peptide hormones, conjugated proteins (i.e., glycopeptides and glycoproteins, lipoproteins, metalloproteins, and others.

"Skin" means the normal, intact skin of a human being or mammal. The skin has a layered construction and consists—as seen from outside to inside—of epidermis, dermis, and subcutis. Within these three components, the skilled person may distinguish further layers.

In the case of the epidermis, five layers are distinguished: the horny layer (stratum corneum), shiny layer (stratum lucidum), granular layer (stratum granulosum), spiny cell layer (stratum spinosum), and basal layer (stratum basale).

"Ablatively treated skin" means the normal, intact skin of a human being of whose epidermis the stratum corneum has—at least partly—been destroyed or removed. In this area of ablatively treated skin, the "proportional area of normal, intact skin of whose epidermis the at least the stratum corneum has been destroyed or removed" (corresponding to the sum of the areas X in FIG. 2) relative to the "total normal, intact skin on whose epidermis the stratum corneum remains" (corresponding to the area A in FIG. 2) may be below 50%, preferably below 20%, and more preferably below 10%. The sections of the epidermis at which the stratum corneum has been removed may be irregular in shape. Preferably, however, they are of defined shape and area. Suitable shapes contemplated include rectangles, hexagons, octagons, squares, circles, and spots. The sections of the epidermis which are removed by ablative treatment have a depth such that at least the stratum corneum is removed at the locations in question and so the "microchannels" are formed beneath the areas X (cf. FIG. 2). The sections of the epidermis removed by ablative treatment are preferably, however, not to extend any deeper than down to the dermis. This can be achieved by means of corresponding adaptation of the laser power and simultaneous check measurements.

The term "transdermal" refers to the route of administration through the skin of a human being or mammal. Skin here means both the normal, intact skin and also the "ablatively treated skin" in the sense of the above definition.

Substances contemplated as the "carrier substance" for the active ingredient layer include substances which behave compatibly in relation to the at least one peptide. It is known that, with peptides, not only chemical influences, such as, for example, acids, salts or organic solvents, but also physical exposures, such as high or low temperatures or else pressure, may alter the secondary and tertiary structure and hence ultimately, also the quaternary structure (denaturing). Denaturing may also cause changes in the physical and physiological properties of the peptides. In the case of chemical cleavage of the peptides (proteolysis), fragments are produced from them, and are called peptones.

As far as the requirements concerning the compatibility of the carrier substance are concerned, this means that, when the peptide is imbedded into the carrier substance, there must be no interaction with the peptide that lead to any such change in the structure of the peptide or to any deterioration otherwise originating of its pharmacological properties.

The effect of the carrier substance is that the at least one peptide is distributed uniformly in the active ingredient layer. The carrier substance preferably has the effect that the peptide molecules are present individually, i.e., in the form of a true "solution".

It has emerged that suitable carrier substances are more particularly those which are "hydrophilic". By hydrophilic ("water-loving") is meant the capacity to bind water or to penetrate water and, in a further sense, "to be wetted effectively by water".

Particularly suitable, therefore, are those carrier substances which possess the capacity to swell on contact with water ("swelling capacity") or which in fact dissolve in water ("water-solubility"). Swelling is the process of altering volume and form of a solid on exposure to water, where water here may be present in the form of a liquid, of a vapor, a gas. If unrestricted swelling occurs, the swelling substance ultimately undergoes transition to form a solution or suspension; where swelling is limited, in contrast, it remains coherent (gel formation).

With cellulose and its derivatives, swelling is understood as the penetration of water molecules into the non-crystalline regions of the cellulose, and the associated spreading of the cellulose chains.

The most suitable carrier substances therefore include more particularly those which have at least one hydrophilic group in the molecule.

Included specifically among the suitable carrier substances are the following:
- $SiO_2$, chemically modified $SiO_2$, more particularly hydrophilic fumed silica of the "AEROSIL®" brand
- polyvinyl alcohol (PVA) and derivatives
- polyvinylpyrrolidone (PVP; e.g., KOLLIDON®, also crosslinked PVP
- polyvinyl alcohol-polyvinylpyrrolidone copolymers
- cellulose and its derivatives, such as methylcellulose, hydroxymethylcellulose, hydroxypropylmethylcellulose, carboxymethylcellulose, ethylcellulose (METHOCEL®, PHARMACOAT®, METOLOSE®)
- polysaccharides such as starch, amylopectin, glycogen, inulin, chitin, pectins, etc.

Mixtures of at least two carrier substances are also possible.

The carrier substance is preferably a substance which is solid at room temperature. Liquid carrier substances may, however, also be used.

The carrier substance may be present in the active ingredient layer in the form of fibers, powder or a film. The carrier substance preferably forms a film having a constant layer thickness. This layer thickness may be between 20 and 200 μm, preferably between 30 and 80 μm.

The active ingredient layer may comprise "buffers" in order to maintain a defined pH therein and to increase the stability of the active ingredient. Buffer systems and the pH values which can be set using them are known to the skilled person.

Layers contemplated as the "backing layer" are occlusive and nonocclusive layers, with the occlusive layers being preferred. These layers are constructed of films/foils, woven and/or knitted fabrics, with films/foils being preferred. The materials involved are natural or synthetic polymers and metals. Particularly preferred are composite materials comprising synthetic polymers and metals in the form of laminates. The backing layer is preferably flexible and impervious for the active ingredient.

The "active ingredient layer" comprises—as already stated—at least one peptide and at least one carrier substance for the peptide. It may have an area of 0.1 to 100 $cm^2$, preferably of 1 to 80 $cm^2$, and more preferably between 2 and 20 $cm^2$. The thickness of the active ingredient layer may be between 20 and 200 μm, preferably between 30 and 80 μm.

The "concentration" of the at least one peptide in the active ingredient layer is heavily dependent on the therapeutic indication, on the activity of the peptide in question, and on its molecular weight. The concentration may therefore vary within wide ranges and in the active ingredient layer may be between 0.1 to 70% by weight, preferably between 1 and 20% by weight.

In order for the active ingredient layer which comprises a peptide and a carrier substance for the peptide to be furnished "pressure-sensitively adhesively", it may be admixed with at least one "pressure-sensitive adhesive". The pressure-sensitive adhesives that are suitable are set out later on below. Another possibility involves furnishing the active ingredient layer pressure-sensitively adhesively by addition of plasticizers, tackifiers, etc. Especially when the carrier substance is highly hydrophilic, it is advantageous to use hydrophilic tackifiers such as pantothenyl alcohol, honey, low-molecular-weight carbohydrates (such as sucrose, glucose, fructose) and derivatives thereof (such as sucrose acetate isobutyrate, for example), and combinations thereof.

In one particular embodiment the active ingredient layer may comprise water. The water content (residual moisture content), however, is preferably low, in order not to jeopardize the mechanical stability of the active ingredient layer and to minimize other risks—more particularly microbiological risks—due to the presence of water. The "water content" in the active ingredient layer is preferably below 20%, more preferably below 10%, and very preferably below 5% and even more preferably below 3%.

The additional "pressure-sensitively adhesive layer" may be constructed from the "pressure-sensitive adhesives" that are known to the skilled person. Pressure-sensitive adhesives are able to induce "wetting", producing sufficient forces of adhesion, at room temperature, without activation by solvent or heat, solely by being pressed onto the surface of the article which is to be stuck.

As "pressure-sensitive adhesives" it is possible to use "polymers" which by virtue of the composition of their monomers possess pressure-sensitively adhesive properties. These include synthetic rubber and natural rubber, butyl rubber, styrene-butadiene copolymers, ethylene-vinyl acetate copolymers, acrylonitrile copolymers, polychloroprene, polyisobutylene, polyvinyl ethers, styrene-butadiene-styrene block polymers, styrene-isoprene-styrene block polymers, polyacrylates, polyesters, polyurethanes, and polysiloxanes. The adhesive properties of the polymer obtained in the polymerization can be modified by functional groups in the monomers of these polymers.

Another way of modifying the adhesive properties of these stated polymers is afforded by the adaptation of the adhesive formula to the desired properties through addition of additives such as resins, plasticizers, tackifiers, fillers and/or stabilizers.

Particularly suitable polymers having pressure-sensitively adhesive properties are polyacrylates, polyisobutylenes, silicones.

It is preferred to use those pressure-sensitive adhesives which are notable for their high physical compatibility with the peptides and which at the same time do not trigger any instances of skin irritation, allergies or sensitization in use.

As the "protective sheet" in the transdermal therapeutic system it is possible to use the films that are known to the skilled person, such as siliconized polyester films, for example.

The use of the transdermal therapeutic system (TTS) which comprises an active ingredient layer and at least one peptide and at least one carrier substance for the peptide is a further solution provided by the invention.

For this purpose, prior to the application of the TTS, the horny layer (the stratum corneum) of the skin is at least sectionally removed, preferably by means of the skin ablation technique. In one preferred embodiment this ablatively treated skin has microchannels in this area within the stratum corneum.

Subsequent application of the TTS allows transdermal absorption of the peptide. For this purpose, the TTS is placed directly onto the ablatively treated skin. The active ingredient layer, comprising the peptide and a carrier substance for the peptide, comes to lie directly above the ablatively treated skin in this case.

Owing to the at least local removal of the stratum corneum, the peptide is able to reach the underlying layers of the skin and ultimately to enter the circulation transdermally. Moisture originating from the layers of the skin below the Stratum corneum may facilitate the transport of the peptide through the at least locally removed sections of the stratum corneum (i.e., through the microchannels).

The additional pressure-sensitively adhesive layer may optionally be used to effect additional fixing of the TTS on the skin.

In one particular embodiment, during the application of the "skin ablation technique", the ablatively treated skin area is marked in color, allowing the subsequent application of the TTS to be performed with precision and ease.

The application time of one application may be from a few hours (for example, 2 to 6 hours) through to one or more (for example, 3 to 7) days. Repeated applications are possible as well. For this purpose, the TTS may be placed onto the ablatively treated skin on which a TTS has already been applied. Preferably the TTS—especially in the case of a relatively long-lasting therapeutic application—is always placed on an area of skin treated ablatively immediately beforehand.

With the transdermal therapeutic system (TTS) comprising a backing layer and an active ingredient layer comprising a peptide and a hydrophilic carrier substance for administering a peptide through ablatively treated skin to a patient, it is possible to treat a person suffering from prostate cancer, endometriosis or premature puberty, the peptide in this case being triptorelin.

With the transdermal therapeutic system (TTS) comprising a backing layer and an active ingredient layer comprising a peptide and a hydrophilic carrier substance for administering a peptide through ablatively treated skin to a patient, it is possible to treat a person who requires assistive fertility therapy, the peptide in this case being triptorelin.

With the transdermal therapeutic system (TTS) comprising a backing layer and an active ingredient layer comprising a peptide and a hydrophilic carrier substance for administering a peptide through ablatively treated skin to a patient, it is possible to treat a person who requires an antidiuretic, who suffers from enuresis nocturna, who requires an antihemorrhagic, who suffers from hemophilia, suffers from uremic thrombocytopathy or suffers from Willebrand-Jürgens syndrome, the peptide in this case being desmopressin.

With the transdermal therapeutic system (TTS) comprising a backing layer and an active ingredient layer comprising a peptide and a hydrophilic carrier substance for administering a peptide through ablatively treated skin to a patient, it is possible to treat a person who requires a highly hypertensive substance or who suffers from diabetes insipidus centralis, the peptide in this case being vasopressin.

The method for producing a transdermal therapeutic system (TTS) for administering peptides, comprising an active ingredient layer which comprises at least one peptide and at least one carrier substance for the peptide, comprises a plurality of steps.

In the first step, the peptide is dissolved, preferably in a corresponding buffer. Particularly suitable solvents contemplated include isotonic saline solution and aqueous buffer solutions having a corresponding pH.

The carrier substance is then likewise dissolved, with appropriate solvents being those such as ethanol, water, and low-boiling solvents. The two solutions are mixed.

Further excipients may be added, such as stabilizers (for example, mannitol), pressure-sensitive adhesives, plasticizers, tackifiers, etc.—either to one of the two solutions (i.e., peptide solution or carrier substance solution) or to the mixture of the two solutions.

The resulting composition can be coated out onto a substrate, with a layer thickness of 10 to 500 µm.

In a further workstep, the layer-form composition thus obtained is dried in order to remove the solvent, preferably down to a desired residual water content of below 20%, more preferably below 10%.

Individual sections can be punched from the resultant active ingredient layer, and are joined by laminating to the backing layer and the protective layer.

Alternatively it is also possible for the further components of the TTS, more particularly the backing layer and the protective sheet, to be joined by laminating to the active ingredient layer produced beforehand.

In one preferred embodiment, the active ingredient layer—optionally also in the form of individual sections—is placed onto an additional layer of pressure-sensitive adhesive and is then joined by laminating with the other components of the TTS—more particularly the backing layer and the protective sheet.

The examples which follow serve for illustration of the invention, without restricting it.

EXAMPLE 1

Triptorelin acetate is dissolved in aqueous acetate buffer solution (pH 5.0). Mannitol is added to this solution until present at a concentration of 3% mannitol. Following addition of ethanolic polyvinylpyrrolidone solution (KOLLIDON® 90 F) and glycerol, a composition is obtained from which, by coating and drying of the solvents (water, ethanol), a uniformly thick film is produced.

The table below shows the composition of the resultant active ingredient layer in the dried state.

| Active ingredient layer | Amount [in g] | Amount [in %] |
| --- | --- | --- |
| Triptorelin acetate | 3.39 | 16.95 |
| Polyvinylpyrrolidone (in solution in ethanol) | 13.47 | 67.35 |
| Glycerol | 2.00 | 10.00 |
| Sodium acetate (trihydrate) | 0.48 | 2.40 |
| Acetic acid | 0.12 | 0.60 |
| Mannitol | 0.54 | 2.70 |
| Purified water | — | — |
| Total: | 20.00 | 100 |

The layer thickness amounts to about 40 µm.

From the dried film, square sheet sections of 5 cm$^2$ are cut, which have a triptorelin content of 3 mg. This corresponds to a loading of 0.6 mg/cm$^2$.

These sheet sections of the active ingredient layer are placed centrally onto a square piece of a backing layer which measures 10 cm$^2$ and is provided on its underside with an additional layer of pressure-sensitive adhesive, 60 µm thick. The material of the layer of pressure-sensitive adhesive comprises a mixture of 85% by weight of a high molecular weight polyisobutylene (Oppanol B 100) and 15% by weight of a medium molecular weight polyisobutylene (Oppanol B 10).

The active ingredient layer and the protruding edges of the layer of pressure-sensitive adhesive are lined using a siliconized polyester film.

EXAMPLE 2

Specimens as per example 1 are produced, with the difference that the loading with triptorelin acetate corresponds to 0.1 mg/cm$^2$, 0.2 mg/cm$^2$, and 0.3 mg/cm$^2$.

EXAMPLE 3

Figure 4:
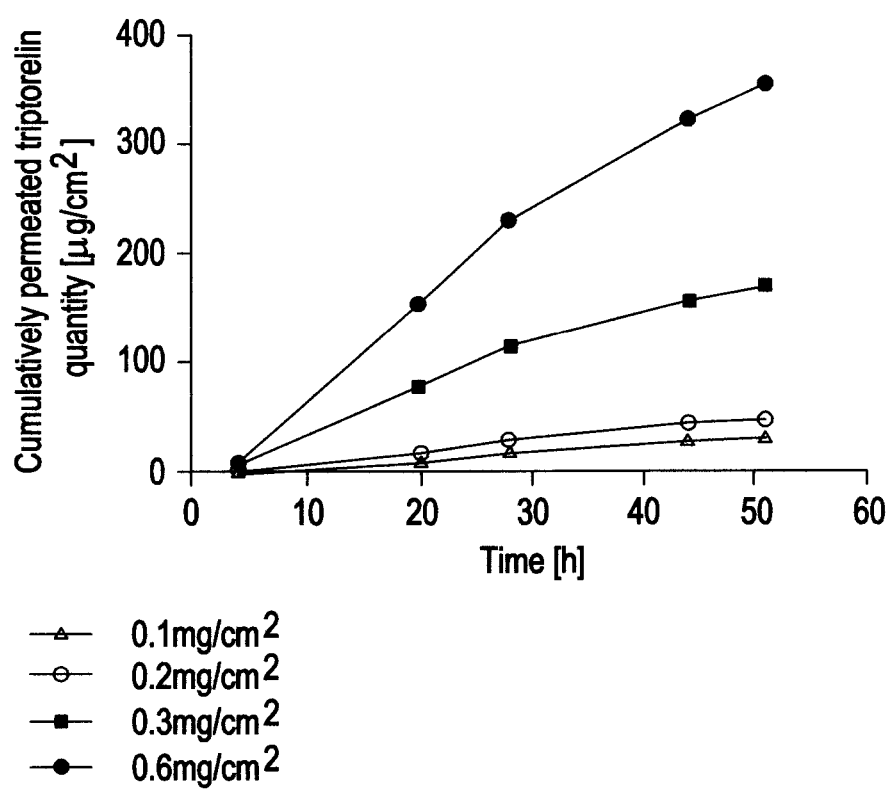
FIG. 4 is a graphical illustration of the effect of the amount of triptorelin on the in vitro permeation as per Examples 1 and 2.

Specimens of the transdermal therapeutic systems produced in examples 1 and 2, with triptorelin acetate as active ingredient, are investigated for their permeation behavior in a Franz diffusion cell. The results of these investigations are shown in FIG. 4, the model membrane used being ablatively laser-pretreated cow udder skin.

DESCRIPTION OF THE FIGURES

Figure 2:
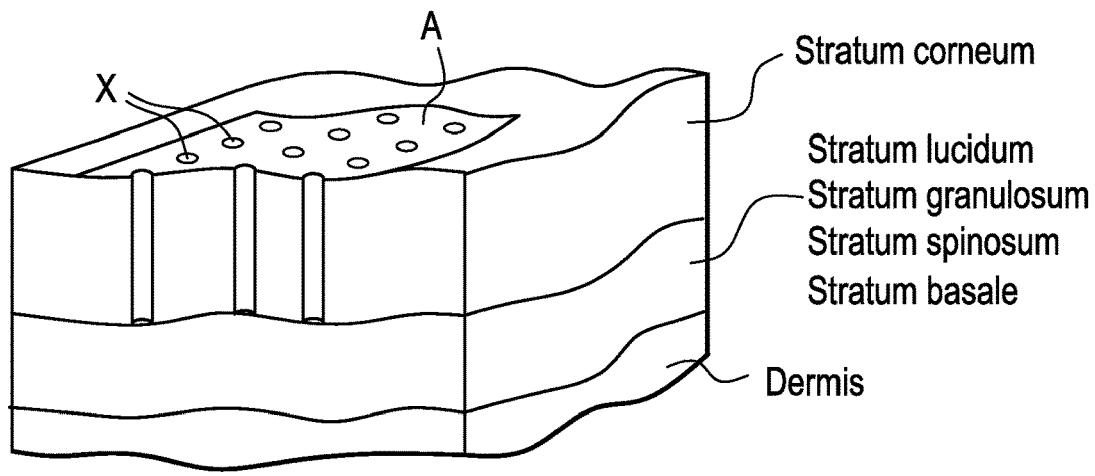
FIG. 2 is a diagrammatic structure of ablatively treated skin.

FIG. 1 shows the diagrammatic structure of intact, normal skin, with an enlarged section of the outermost layer. Definitions therein are as follows:
E=epidermis
D=dermis
S=subcutis
B=blood vessel
s.c.=stratum corneum
s.l.=stratum lucidum
s.gr.=stratum granulosum
s.sp.=stratum spinosum
s.b.=stratum basale FIG. 2 shows the diagrammatic structure of ablatively treated skin. Here, A denotes the ablatively treated area of skin, and X the areas at which the stratum corneum has been removed.

Figure 3:
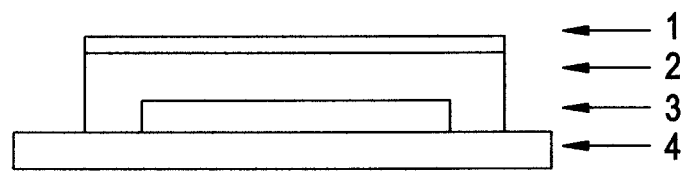
FIG. 3 is a diagrammatic structure of an exemplary inventive transdermal therapeutic system.

FIG. 3 shows the diagrammatic structure of a transdermal therapeutic system as per example 1. Definitions are as follows: 1=backing layer, 2=continuous layer of pressure-sensitive adhesive, 3=active ingredient layer, 4=protective sheet.

FIG. 4 shows the effect of the amount of triptorelin on the in vitro permeation as per examples 1 and 2. The permeation barrier used for the investigations was ablatively treated 1 200 μm-thick dermatomized cow udder skin.

The invention claimed is:

1. A transdermal therapeutic system (TTS) for administering a peptide onto ablatively treated intact living skin whose epidermis has had its stratum corneum at least partially destroyed or removed comprising (i) an occlusive backing layer furnished with a layer of pressure-sensitive adhesive rendered adhesive by its monomer composition, (ii) at least one active ingredient layer comprising at least one peptide in solution in a film formed from a carrier substance consisting of a hydrophilic carrier selected from polyvinyl alcohol, polyvinylpyrrolidone, polyvinyl alcohol-polyvinylpyrrolidone copolymers, polysaccharides, derivatives or mixtures thereof and (iii) a protective sheet that lines the active ingredient layer before the TTS is employed,
wherein said peptide has a molecular weight of more than 500 Da,
wherein said pressure-sensitive adhesive, placed between said backing layer and said active ingredient layer, has an area greater than the area of said active ingredient layer such that said pressure-sensitive adhesive ensures adhesion of the TTS to the skin
wherein said active ingredient layer is disposed adjacent said protective sheet,
said carrier substance forms a constant layer thickness film,
and the active ingredient layer comprises additives rendering the hydrophilic carrier substance pressure-sensitive consisting of plasticizers or tackifiers.

2. The TTS as claimed in claim 1, wherein the peptide is an oligopeptide, a polypeptide, a protein, an isopeptide, a peptide hormone or a combination thereof.

3. The TTS as claimed in claim 1, wherein the peptide is a glandular peptide hormone of a hypophysis, a releasing hormone of a hypothalamus, an inhibiting factor of a hypothalamus, a peptide hormone from a pancreas, a peptide hormone from a stomach or a peptide hormone from a gut or a pharmaceutically acceptable salt thereof.

4. The TTS as claimed in claim 1, wherein the peptide is triptorelin, desmopressin or vasopressin or a pharmaceutically acceptable salt thereof.

5. The TTS as claimed in claim 1, wherein the peptide is present in a concentration of 0.1 to 70% by weight in the active ingredient layer.

6. The TTS as claimed in claim 1, wherein the active ingredient layer has a water content below 20%.

7. The TTS as claimed in claim 1, wherein the active ingredient layer has an area of 0.1 to 100 cm$^2$ and a thickness of between 20 and 200 μm.

8. A method for producing the TTS as claimed in claim 1; said method comprising:
a. mixing the peptide with a solution of the hydrophilic carrier substance,
b. spreading the composition thus obtained in a constant thickness on an underlayer,
c. drying the spread composition to a predetermined water content of below 20%, to form the at least one active ingredient layer, and
d. producing individual sections of the at least one active ingredient layer and joining them to the backing layer.

9. The method as claimed in claim 8, wherein the individual sections of the at least one active ingredient layer are joined to the backing layer by the layer of pressure-sensitive adhesive.

10. A method for the treatment of prostate cancer, endometriosis, premature puberty or a woman as part of assistive fertility therapy comprising applying the transdermal therapeutic system (TTS) as claimed in claim 1 including the backing layer and the at least one active ingredient layer comprising the peptide triptorelin or a pharmaceutically acceptable salt thereof, wherein said method further comprises, in a first step, ablatively treating normal, intact skin of a person to be treated and, in a further step, adhering the TTS to the ablatively treated skin to deliver the peptide transdermally.

11. A method for the treatment of a person who requires an antidiuretic and suffers from Enuresis nocturna, who requires an antihemorrhagic, suffers from hemophilia, suffers from uremic thrombocytopathy or suffers from Willebrand-Jürgens syndrome-comprising applying the transdermal therapeutic system (TTS) as claimed in claim 1 including the backing layer and the at least one active ingredient layer comprising the peptide desmopressin or a pharmaceutically acceptable salt thereof, wherein said method further comprises, in a first step, ablatively treating normal, intact skin of the person to be treated and, in a further step, adhering the TTS to the ablatively treated skin to deliver the peptide transdermally.

12. A method for the treatment of a person who requires a highly hypertensive substance or suffers from diabetes insipidus centralis comprising applying the transdermal therapeutic system (TTS) as claimed in claim 1 including the backing layer and the at least one active ingredient layer comprising the peptide vasopressin or a therapeutically acceptable salt thereof, wherein said method further comprises, in a first step, ablatively treating normal, intact skin of the person to be treated and, in a further step, adhering the TTS to the ablatively treated skin to deliver the peptide transdermally.

13. A transdermal therapeutic system (TTS) for administering a peptide for 3 to 7 days onto ablatively treated intact living skin whose epidermis has had its stratum corneum at least partially destroyed or removed consisting of either
- (i) a backing layer, (ii) an active ingredient layer having a carrier substance, peptide(s) in solution therein, and additives sufficient to render the carrier pressure-sensitively adhesive, (iii) a protective sheet that lines the active ingredient layer before the TTS is employed and (iv) a pressure-sensitive adhesive layer disposed between the carrier substance and the backing layer or
- (v) a backing layer, (vi) a protective sheet that, lines the active ingredient layer before the TTS is employed and (vii) a pressure-sensitive-adhesive active ingredient layer consisting of a coating containing carrier substance, an active ingredient consisting of peptide(s) in solution therein, and additives selected from plasticizers or tackifiers sufficient to render the carrier substance pressure-sensitively adhesive,
- wherein the carrier substance consists of polyvinylpyrrolidone but not crosslinked polyvinylpyrrolidone and is in the form of a full-area constant layer thickness film,
- and the pressure-sensitive adhesive layer is rendered adhesive by its monomer composition.

14. The TTS as claimed in claim 13, wherein the carrier substance is polyvinylpyrrolidone having a molecular weight between 790 000 and 1 500 000 Da.

15. The TTS as claimed in claim 5, wherein the peptide is present in a concentration of between 1 and 20% by weight in the active ingredient layer.

16. The TTS as claimed in claim 13, wherein the active ingredient layer has a water content below 10%.

17. The TTS as claimed in claim 6, wherein the active ingredient layer has a water content below 5%.

18. The TTS as claimed in claim 7, wherein the active ingredient layer has an area of 1 to 80 cm$^2$ and a thickness of between 30 and 80 μm.

19. The TTS as claimed in claim 7, wherein the active ingredient layer has an area of from 2 to 20 cm$^2$.

20. A method as claimed in claim 8, wherein the dried spread composition has a water content of below 10%.

21. A transdermal therapeutic system as claimed in claim 10, wherein the skin is ablatively treated by laser and the peptide is delivered over a period of at least 2 hours.

22. A transdermal therapeutic system as claimed in claim 11, wherein the skin is ablatively treated by laser and the peptide is delivered over a period of at least 2 hours.

23. A transdermal therapeutic system as claimed in claim 12, wherein the skin is ablatively treated by laser and the peptide is delivered over a period of at least 2 hours.

24. A transdermal therapeutic system (TTS) as claimed in claim 1, wherein the ablatively treated intact skin contains a proportional area of skin whose stratum corneum has been destroyed or removed of below 50% and the ablative treatment forms microchannels within the stratum corneum.

25. The TTS as claimed in claim 1, wherein said TTS further comprises microinjection needles, microblades, needles and/or barbs.

26. A transdermal therapeutic system for administering a peptide onto ablatively treated intact living skin whose epidermis has had its stratum corneum at least partially destroyed or removed comprising (i) a single, occlusive backing layer, (ii) at least one active ingredient layer comprising at least one peptide in solution in a hydrophilic carrier substance forming a constant layer thickness film that swells to form a gel and additives sufficient to render the carrier substance pressure-sensitively adhesive, a pressure-sensitive adhesive placed between said backing layer and said active ingredient layer, having an area greater than the area of said active ingredient layer such that said pressure-sensitive adhesive ensures adhesion of the TTS to the skin and (iv) a protective sheet that lines that active ingredient layer before the TTS is employed,
- wherein the hydrophilic carrier substance is not polyacrylate or crosslinked polyvinylpyrrolidone and
- the additives rendering the hydrophilic carrier substance pressure-sensitive consists of plasticizer or tackifier,
- the hydrophilic carrier substance has polyvinylpyrrolidone along with acetic acid and sodium acetate trihydrate;
- and the pressure-sensitive adhesive layer is rendered adhesive by its monomer composition.

27. A transdermal therapeutic system as claimed in claim 1, wherein the hydrophilic carrier substance is crosslinked polyvinylpyrrolidone.

28. A transdermal therapeutic system as claimed in claim 1, wherein said additives rendering the carrier substance pressure-sensitively adhesive consist of glycerol, medium-chain triglycerides or hydrocarbons.

29. A transdermal therapeutic system as claimed in claim 13, wherein the layer of pressure-sensitive adhesive is continuous.

30. A transdermal therapeutic system as claimed in claim 13, wherein the backing layer is occlusive and the additives in the active ingredient layer comprise glycerol.

\* \* \* \* \*

UNITED STATES PATENT AND TRADEMARK OFFICE
CERTIFICATE OF CORRECTION

PATENT NO. : 10,772,845 B2
APPLICATION NO. : 13/512403
DATED : September 15, 2020
INVENTOR(S) : Horstmann et al.

It is certified that error appears in the above-identified patent and that said Letters Patent is hereby corrected as shown below:

On the Title Page

Item [56], References Cited, FOREIGN PATENT DOCUMENTS delete "WO 2010/0028412 A2" and insert --WO 2008/095597 A2--

In the Claims

Column 13, Line 19 delete "a protective sheet that, lines" and insert --a protective sheet that lines--

Signed and Sealed this
Twenty-ninth Day of December, 2020

Andrei Iancu
*Director of the United States Patent and Trademark Office*